United States Patent [19]

Edwards

[11] 4,357,172

[45] Nov. 2, 1982

[54] PROCESS FOR CONTINUOUS CRYSTALLIZATION OF ALPHA MONOHYDRATE DEXTROSE UTILIZING HIGH AGITATION

[75] Inventor: Larry W. Edwards, Hillsdale, N.J.

[73] Assignee: CPC International Inc., Englewood Cliffs, N.J.

[21] Appl. No.: 217,484

[22] Filed: Dec. 17, 1980

[51] Int. Cl.$^3$ .............................................. C13F 1/02
[52] U.S. Cl. ....................................... 127/60; 127/30
[58] Field of Search ........................ 127/15, 16, 30, 60

[56] References Cited

U.S. PATENT DOCUMENTS

| | | | |
|---|---|---|---|
| 1,521,830 | 1/1925 | Newkirk | 127/60 |
| 3,257,665 | 6/1966 | Idaszak | 127/60 |
| 3,607,392 | 9/1971 | Lauer et al. | 127/30 |

*Primary Examiner*—Michael S. Marcus

[57] ABSTRACT

A process for continuously crystallizing alpha monohydrate dextrose from dextrose-containing liquours. The process is operated isothermally and produces a lean phase massecuite. According to the process, a rate of agitation is employed, within a reaction zone operated in a continuous mode, which permits linear growth of crystals to occur at a growth rate which is surface reaction controlled. The process may be combined with a batch process by feeding lean phase massecuite from the process into a second reaction zone operated in a batch mode. This is done at a constantly declining temperature and produces a rich phase massecuite. The batch process stage is also continuously agitated, but at a slower rate than the first stage continuous process to prevent excessive attrition of existing crystals while maximizing crystal yield.

5 Claims, 1 Drawing Figure

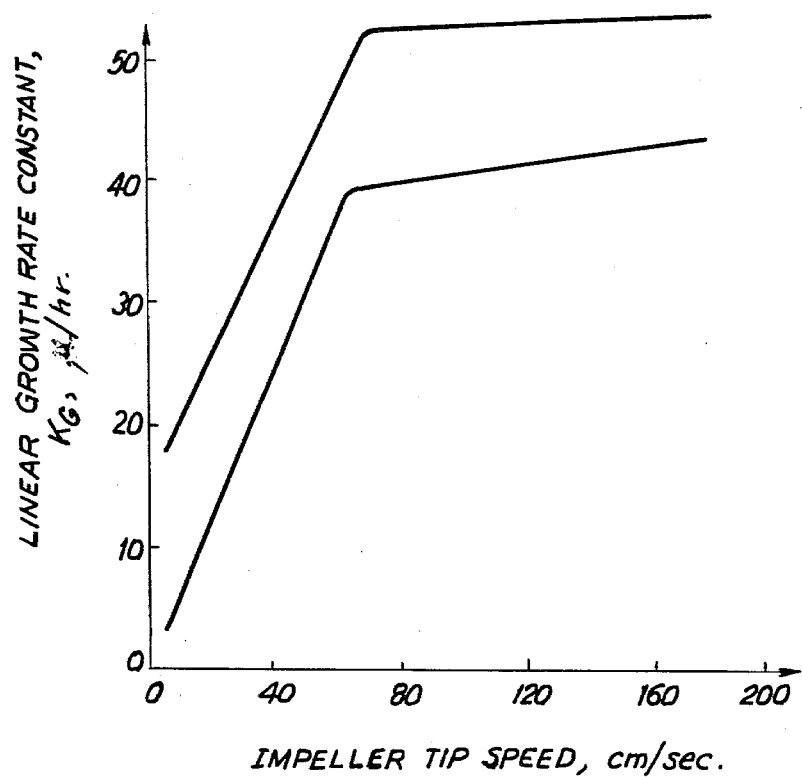

PROCESS FOR CONTINUOUS CRYSTALLIZATION OF ALPHA MONOHYDRATE DEXTROSE UTILIZING HIGH AGITATION

BACKGROUND OF THE INVENTION

1. Field of the Invention

This invention relates to an improved process of crystallizing dextrose monohydrate. More particularly, this invention relates to a continuous crystallization process which rapidly forms a lean phase massecuite and a two-stage, continuous-batch process which produces a rich phase massecuite.

2. Description of the Prior Art

It is known and recognized that dextrose can exist in three crystalline forms, the alpha hydrate form, the alpha anhydrous form, and the beta anhydrous form. The alpha anhydrous and beta anhydrous forms are developed from super-saturated solutions of dextrose at elevated temperatures whereas the hydrate form is unique in that it only forms from super-saturated solutions at relatively low temperatures. The temperature at which dextrose hydrate crystallization begins in a hot super-saturated solution of dextrose having the proper moisture content is shown in the Corn Refiner's Association Critical Data Table. Therein, the transition point between hydrate and anhydrous dextrose is given as 50° C. and the percent dextrose is given as 70.91, working with dextrose solutions in pure water. However, in commercial practice, the starch hydrolysates contain small amounts of non-dextrose substances which modify the transition point; therefore, it is preferable to designate a transition range which in this case is from about 50° C. to about 55° C.

The commercial process for producing dextrose hydrate developed by W. B. Newkirk, in the early 1920's, is still in use today. The basic principles of this process are set forth in U.S. Pat. Nos. 1,471,347; 1,508,569; 1,521,830. The object of the Newkirk process was to obtain dextrose hydrate crystals, designated as purgeable crystals, from which the hydrol or mother liquor could be removed by centrifuging and washing.

In commercial practice of the Newkirk process, the dextrose hydrate crystals are produced by contacting a dextrose containing solution or liquor with dextrose hydrate seed crystals under crystallization temperatures in a crystallizer. A massecuite is formed which consists of a mixture of crystals and mother liquor. Twenty to thirty percent of the massecuite from a previous crystallization is used in the form of a mass of seed crystals in each succeeding crystallization. The crystallizer is rapidly filled with dextrose-containing liquor produced by the acid or enzymic hydrolysis of starches. The temperature of the dextrose liquor is from 40° C. to 60° C. The temperature of the mixture of dextrose liquor and crystals from the previous crystallization is 35° C. to 55° C., and the temperature of the massecuite at the completion of crystallization is 20° C. to 35° C. The mixture is kept at the temperature of mixing until part of the dextrose has crystallized and the initially very high super-saturation is reduced. The massecuite is subsequently cooled in the crystallizer to the centrifuging temperature with concomitant further crystallization of dextrose. The conventional crystallization process is accordingly performed as one batch operation, in one vessel, and at a continuously decreasing temperature.

Even with thorough mixing of the dextrose liquor and the mass of crystals, the super-saturation is so high at the beginning of crystallization that the formation of minute new crystals occurs in addition to the continued growth of the crystals already present. These minute new crystals are often produced in such a great number that there is not sufficient D-glucose in solution in the dextrose liquor available to continue the growth of the dextrose crystals to the desired size until the completion of the crystallization. The massecuite thus consists of crystals of widely differing size and is therefore often very difficult to centrifuge. Large crystals facilitate centrifuging because the apparent viscosity of the massecuite containing large crystals is lower than that of a massecuite consisting only of minute crystals or of crystals of widely differing size. The larger the crystals are, the smaller is their surface per unit of weight. Less wash water is required to wash away the mother liquor, which reduces yield losses caused by dissolution of the crystals during centrifuging.

Other disadvantages of the Newkirk process as a commercial practice today are the long periods of time required for crystallization of the rich phase massecuite product. This problem is exacerbated by need to leave 20–25% of crystals in each crystallizer as seed for subsequent crystallizations. The long crystallization times necessitate a large capital investment for equipment and housing. For example, in commercial practice, the average crystallizing time required to form the dextrose hydrate from the dextrose containing liquor is between 40 and 120 hours. The time and labor required for filling and emptying the crystallizers, as well as for maintenance of such equipment, of course, adds more to the cost of operating present commercial systems. Moreover, there is an in-plant sanitation problem which increases the cost still more. It will be readily apparent that there is a long-felt need and desire to provide a more simple and more economical process for obtaining dextrose hydrate.

SUMMARY OF THE INVENTION

1. Objects of the Invention

It is therefore an object of this invention to provide a process for continuously crystallizing alpha monohydrate dextrose from dextrose-containing liquors.

It is also an object of this invention to provide an improved continuous process for the production of alpha monohydrate dextrose which process is more advantageous than prior art processes.

Another object of this invention is to provide an alpha monohydrate dextrose by a continuous process which can be readily carried out in a minimum amount of processing time.

Another object of this invention is to provide a continuous process for crystallizing alpha monohydrate dextrose which eliminates the need for leaving a 20–25% seed bed in the costly batch crystallizers, thereby improving productivity.

A further object of this invention is to provide a continuous process for crystallizing alpha monohydrate dextrose wherein the process conditions can be varied and automatically controlled to produce a desired composition of sugar product.

These and other objects of the invention will become apparent in light of the following description of the process of this invention.

2. Brief Description of the Invention

Briefly, the present invention provides a process for continuously crystallizing alpha monohydrate dextrose from a dextrose-containing liquor. The process is operated isothermally and produces a lean phase massecuite.

In a preferred embodiment of the invention, the continuous crystallization process is operated as a first stage in a two stage process. The second stage is a batch process that produces a rich phase massecuite. The principles of this invention are illustrated by the description of this preferred embodiment which follows.

In the continuous stage of this process, a dextrose-containing liquor feed is introduced into a first reaction zone comprised substantially of lean phase massecuite having a mean residence time from about 6 to about 30 hours. The reaction zone is continuously agitated at a preselected rate. Such rate of agitation permits linear crystal growth of the feed to occur at a growth rate which is surface reaction controlled. Such rate of agitation also avoids excessive attrition of the lean phase massecuite in the reaction zone. The temperature at which crystallization occurs in the first stage is fixed between about 40° C. and 50° C. The agitation of the reaction zone results in the feed in the continuous stage being rapidly and intimately admixed with the lean phase massecuite. The crystal content of the lean phase massecuite bed provides seed crystals for crystallization of the dextrose liquor feed. The operating conditions of the reaction provide for optimum rate of crystal growth.

In the batch (i.e., second) stage, lean phase massecuite from the continuous stage is introduced into a subsequent reaction zone. The reaction zone is continuously agitated at a rate substantially slower than in the continuous stage to prevent excessive crystal attrition. This rate provides a linear crystal growth rate which is diffusion controlled.

The crystal content of the lean phase massecuite product of the continuous stage provides seed crystals for further crystallization of the lean phase massecuite in the batch stage to produce a rich phase massecuite. The time to complete the crystallization of the lean phase massecuite to the rich phase massecuite product of the batch stage varies from about 6 hours to about 30 hours.

In the following discussion, the two stages of the process of the invention are explained in more detail.

3. Detailed Description of the Invention

A lean phase massecuite is obtained by crystallizing a supersaturated D-glucose solution, e.g. a dextrose liquor having a dry substance content of from 70 to 85% at a constant temperature in the range of from about 35° C. to about 50° C. The dextrose containing liquor may be obtained from acid and/or enzyme hydrolysis of starch, remelted crude dextrose, remelted pure dextrose, and combinations thereof. The dextrose containing liquor is refined and concentrated in a conventional manner to a suitable density range, e.g., from less than saturation at 35° C. to about 85% dry substance at 50° C. and 0.2 supersaturation. Crystallization occurs in a continuous reaction zone which comprises an agitated bed of lean phase massecuite. The rate of agitation is preselected to provide a rate of crystallization of alpha monohydrate dextrose which is controlled by the rate at which the surface reaction occurs, as opposed to diffusion control.

It has been discovered that crystal growth kinetics for the alpha monohydrate dextrose is directly affected by the agitation of the lean phase massecuite in the continuous stage. Growth on existing crystals is a two-step process. First, a solute molecule must diffuse from the bulk of solution, through a laminar film surrounding the crystal, to the crystal surface. Second, once the solute molecule reaches the crystal surface, it must orient itself into the crystal lattice. The rate of linear crystal growth may thus be diffusion controlled or surface reaction controlled. Linear growth rate, G, has been correlated by the following equation disclosed by A. D. Randolph et al. infra:

$$G = K_G s^m$$

wherein $K_G$ = growth rate constant cm/hr.
m = order of growth
s = supersaturation The growth rate constant $K_G$ can be a function of temperature, solution purity and the degree of agitation.

It has been found through experimental tests using turbine blades to produce agitation of a lean phase massecuite bed reaction zone that an impeller tip speed of about 60 cm/sec separates the regions of surface reaction and diffusion-controlled crystal growth. Below this tip speed, crystal growth rate was found to increase with agitation speed. Above this tip speed, little increase in crystal growth rate was observed. Through further testing, however, it has been found that tip speeds in the range of 300–600 cm/sec offer a reasonable compromise with regard to growth rate, nucleation rate, and cost-efficient mechanical agitation design. Crystal attrition (at tip speeds between 300 and 600 cm/sec) was not found to be detrimental to operation of the system.

The crystal size distribution (CSD) present in a crystallizing massecuite is determined by the relative rates of nucleation and growth. The phase change from the liquid to the solid state may occur only in the presence of supersaturation, which may be brought about either by, in most cases, reducing the temperature or increasing the concentration. This phase change may occur by one of two processes: (1) the formation of a new crystal (nucleation), or (2) growth on an existing crystal. Nucleation may be divided into three classes, homogeneous, heterogeneous and secondary. Homogeneous nucleation results from supersaturation only. Heterogeneous nucleation results from the presence of some foreign insoluble material. Secondary nucleation is induced by the mechanical energy input of crystal-crystal collisions. In addition, new crystals may be formed by attrition (no phase change involved), the result of mechanical degradation of existing crystals yielding crystal chips which then begin growing.

According to the process of applicant's invention, nucleation is controlled in the continuous stage so that the primary mode of nucleation is secondary. It is considered that homogeneous nucleation will not be significant providing crystallization occurs in the metastable zone, that region between the unsaturated and labile zones. Attrition is also minimized by control of the agitation rate, assuming that any new crystals formed by crystal-crystal contact are near-nucleus sized (microattrition) and that the parent crystal size is not significantly reduced. Secondary nucleation represents controlled nucleation as opposed to uncontrolled homogeneous, or spontaneous, nucleation, which is triggered by high supersaturation. Controlled nucleation is desired in commercial practice, as it promotes larger and more uniform crystal size and, therefor, easier separation.

Secondary nucleation has been experimentally correlated by A. D. Randolph et al., Theory of Particulate Processes, 1971, by the following equation:

$$B° = k_N M_T^j s^p$$

wherein

B° = nucleation rate, number/hr. cc massecuite
$k_N$ = nucleation rate constant
$M_T$ = mass suspension density (grams crystals/cc massecuite)
j = order of nucleation (suspension)
s = supersaturation
p = order of nucleation (supersaturation).

The rate constant, $k_N$, will depend on temperature, agitation, and presence of impurities. Usually, the exponent j can be taken as unity. See, e.g., M. A. Larson et al., "Crystallization Design Techniques Using the Population Balance," presented at Crystallization Technology Course (The Center for Professional Advancement) Dec. 3-5, 1975.

The rate of crystallization (mass growth) and the product CSD can be experimentally determined using the above equations and determining the rate constants and exponents applicable for the conditions employed. When temperature, purity, and suspension density, and thus the crystal growth and nucleation rates, are changing throughout the cycle, the rate constants will vary and can be experimentally determined.

As mentioned previously herein, it has been found that as crystal growth moves from diffusion to surface reaction control, the basic nucleation mechanism does not change; the rate of nucleation continues to increase while the growth rate levels off. This combination of effects causes the average size of crystals to decrease, which can be expected to increase the difficulty of separation. Thus, the faster one tries to crystallize dextrose, the smaller will be the resulting crystal size and the more difficult the subsequent crystal-mother liquor separation.

According to the process of this invention, feed liquor is charged to a continuous reaction zone comprised of an agitated bed of lean phase massecuite. The rate of agitation is preselected to provide a crystal growth rate which is surface reaction controlled. Along with the rate of agitation, the geometry of the crystallization vessel itself will be such as to enhance the degree of mixing, while maintaining low shear. A suitably baffled, cylindrical tank with an agitator having one or more impellers on a vertical shaft is suitable. For example, when agitation is provided by the rotation of turbine blades along the central axis of the reaction zone, a vertical draft tube situated within the central portion of the reaction zone permits high speed agitation to occur in the vicinity of the central axis without substantial shearing of the particles. Means to remove the heat of crystallization are required. These may include jackets or coils.

Crystals of dextrose start forming soon after the addition of the feed liquor to the continuous reaction zone. This crystal formation is allowed to continue until the crystal phase yield is between about 15% and 45%. As soon as the desired crystal yield is obtained, lean phase massecuite (15-45% crystal phase yield) is continuously discharged while simultaneously being replaced with fresh feed liquor so that the overall concentration and supersaturation of the liquor with respect to dextrose is maintained constant.

The lean phase massecuite withdrawn from the continuous reaction zone of this invention is fed into a second reaction zone, i.e., a different crystallizer. This second stage, batch-type crystallizer is slowly agitated. Agitation is effected by slow rotation of cooling coils situated along a central axis of the batch reaction zone at a slow rate which prevents excessive crystal attrition, but permits heat transfer between the cooling coils and the bulk of the massecuite. When the crystal phase yield of the massecuite within the batch reaction zone reaches about 60%, the rich phase massecuite thereby produced is withdrawn.

The rich phase massecuite is separated into crystals and mother liquor, e.g., by centrifuging, whereupon the crystals are recovered and the mother liquor concentrated by evaporation either for sale or for subsequent use as a feed liquor into the continuous (i.e., first stage) reaction zone in order to obtain an improved yield of crystallization. As a result of the higher growth rates and elimination of seed bed requirements for the aforementioned process, a reduction of up to 40% of the crystallization volume required by the commercial Newkirk batch crystallization process is realized.

One or more continuous reaction zones may be used to supply lean phase massecuite for use in the batch reaction zone.

Known means are provided for removal of lean phase massecuite at a predetermined rate from the continuous stage and simultaneous introduction of feed liquor to the continuous stage. Withdrawal of lean phase massecuite may be rapid and comprise up to about ⅓ of the total volume of lean phase massecuite.

The batch reaction zone can be operated by rapid filling of an empty crystallizer, holding with agitation and cooling until the desired temperature and crystal phase content are reached and subsequently completely emptying the crystallizer.

The amount of seed required to provide either the lean phase or to initially begin the lean phase crystallization process is readily ascertainable by those skilled in the art and is governed more by the number of crystals or nuclei than the weight of the seed. Generally, about 3% to 15% of seed, based on dry substance of the feed liquor, is satisfactory. A preferred amount is 3-4% of seed, based on dry substance of the feed liquor.

The term "crystal phase yield" as used throughout this specification means the product of the weight of the dextrose crystals (anhydrous basis) multiplied by 100 when such product is divided by total weight of dry substance in the massecuite.

The term "supersaturation" as used herein means that the feed liquor is supersaturated with respect to dextrose on an impurity free basis. Supersaturation at temperature T is defined as: $(C/C_O - 1)$ = supersaturation, wherein:

C = unit by weight of dextrose per unit by weight of water at operating temperature T
$C_O$ = unit by weight of dextrose per unit by weight of water in equilibrium at temperature T In the continuous reaction zone of applicant's process, the dextrose crystals are completely surrounded by mother liquor. While not wishing to be bound by such explanation, it is believed that at some point in the crystallization step, the crystals usually fill all the volume in the crystallizers. The mother liquor occupies at this time only the void space. Generally, this occurs in the range of about 45% to 50% crystal phase. Above this crystal phase, two phenomena occur. In one instance, there is breakage of a portion of the large crystals into smaller particles so as to allow them to fit in the void spaces between the remaining large crystals. The other occurrence is further crystallization of only small crystals within the remaining void space. This theory has been borne out by data showing linear viscosity buildup of dextrose massecuites until about 45% crystal phase. Above about 45%-50% crystal phase massecuite, viscosity increased at about a four times greater degree than below this range, indicating a definite change in the nature of the massecuite at about a 45%-50% crystal phase.

It has been found that very minimal crystal loss occurs when the lean phase massecuite is fed in the batch reaction zone where the lean phase massecuite is further crystallized until a rich phase massecuite is obtained.

A distinct advantage of applicant's crystallization process is that operation of the continuous stage of the process may be carried out at constant conditions once equilibrium is established. Continuous crystallization of dextrose liquor in the continuous stage of applicant's process enables an operator to choose a specific operating condition which, once equilibrium is established, can be maintained with commercially available control apparatus for insuring the constancy of such operating parameters such as feed rate, temperature, pressure, level, etc. The constancy of the properties of lean phase product of the continuous stage can be controlled to provide increased uniformity and size of crystals, as well as other massecuite characteristics such as crystal phase yield and temperature.

As pointed out above, the continuous stage of the crystallization process of this invention can be employed to produce a lean phase massecuite from a hydrolyzate. The massecuite may be separated to produce alpha monohydrate dextrose and a mother liquor stream for further processing. According to this embodiment, hydrolyzate of high purity (96-99% d.b. dextrose) can be rapidly crystallized to provide a mother liquor stream product of high enough quality to be sold commercially as a high dextrose corn syrup. It could also be processed through a high fructose corn syrup channel.

The following example is typical and informative and is intended to further illustrate the invention, but is not to be considered as limiting the invention in any manner.

EXAMPLE I

Three identical crystallizers were used. Each crystallizer had the following characteristics: an operating volume of 37.85 liter (10 gal.); liquid depth of 53.1 cm (20.9 in.); a tank diameter of 29.6 cm (11.65 in.); 2-4 blade 45° pitch turbine impellers each having a diameter of 20.3 cm (8 in.) and a blade width of 5.1 cm (2 in.); an agitator sheave diameter of 12.1 cm (4.75 in.) and a variable speed drive range of 95-570 rpm. Massecuite temperature was maintained by means of jacketing and tracing.

The 45°-pitched, 4-blade turbine increased mass transfer near the crystallizer walls with a minimum of shear. For tip speed calculations, commercial practice was determined using a 2.9 meter (9.5 ft.) diameter batch crystallizer of the type described in U.S. Pat. No. 3,762,947 operating at 0.3 rpm, giving a tip speed of about 4.6 cm/sec. (9 ft/min.). Tip speed was varied from 64 to 176 cm/sec. through the tests.

Auxiliary equipment included tanks to hold feed liquor in solution and a vacuum sampling system. This sampling system was designed to remove representative massecuite samples from near the middle of the crystallizer, as an alternative to bottom or overflow discharge. Crystallizer feed liquors of various ash and dextrose concentrations were prepared by adjusting a hydrolyzate of starch made by wholly enzymic processes with anhydrous dextrose and sodium chloride salt. This liquor was adjusted with demineralized water to a dry substance compatible with the crystallization temperature. During the test, feed liquor was maintained above the saturation temperature; solution dry substance was monitored by refractive index and adjusted by addition of demineralized water to balance the loss of water by evaporation.

Each test was started by charging each crystallizer with 30 liters (7.9 gallons), the nominal residence volume, of feed liquor. Continuous operation was simulated by hourly withdrawal of a specified volume of massecuite through the vacuum system mentioned hereinabove, followed by addition of a like volume of feed liquor. The volume transferred was calculated to give the desired residence time.

For each test, the massecuite was allowed to spontaneously nucleate. In general, the crystal phase yield tended to equilibrate after 3-5 residence times of operation; the crystal size distribution required somewhat longer to equilibrate. Test durations generally ranged from 90-115 hours. The following Table I summarizes test data obtained during this series of tests:

TABLE I

| 30° C. 64 cm/sec. Impeller Tip Speed | | | |
|---|---|---|---|
| Test No. | Residence Time, Hours | Crystal Phase Yield, % | Supersaturation Decimal Fraction |
| 1 | 10 | 12.5 | 0.112 |
| 2 | 20 | 17.5 | 0.093 |
| 3 | 30 | 22.0 | 0.070 |
| 38° C. | | | |
| Test No. | Residence Time, Hours | Impeller Tip Speed, cm/sec | Crystal Phase Yield, % | Supersaturation dec. Fraction |
| 3 | 15 | 64 | 35.9 | 0.042 |
| 4 | 15 | 101 | 36.9 | 0.036 |
| 5 | 15 | 176 | 37.5 | 0.032 |
| 6 | 10 | 64 | 32.9 | 0.064 |
| 7 | 10 | 101 | 34.6 | 0.049 |
| 8 | 10 | 176 | 35.2 | 0.046 |
| 48° C. | | | | |
| 9 | 16 | 64 | 37.5 | 0.025 |
| 10 | 16 | 101 | 40.0 | 0.015 |
| 11 | 10 | 64 | 32.0 | 0.047 |
| 12 | 10 | 101 | 34.5 | 0.037 |
| 13 | 10 | 176 | 36.5 | 0.030 |
| 14 | 10 | 64 | 33.6 | 0.046 |
| 15 | 10 | 64 | 33.9 | 0.045 |
| 16 | 10 | 176 | 35.5 | 0.039 |
| 17 | 20 | 64 | 37.2 | 0.032 |
| 18 | 10 | 64 | 30.5 | 0.056 |
| 19 | 7.5 | 64 | 25.0 | 0.071 |

The FIGURE represents the correlation between impeller tip speed and the linear crystal growth rate constant, $K_G$, at 38° C. and 48° C. It is the increase in agitation speed from an impeller tip speed of about 5 cm/sec, which is typical of commercial practice, to about 60 cm/sec, which is believed to enhance the crystallization kinetics.

While certain representative embodiments and details have been shown for the purpose of illustrating the invention, it will be apparent to those skilled in the art that various changes and modifications may be made therein without departing from the spirit or scope of the invention.

What is claimed is:

1. A process for continuously crystallizing alpha monohydrate dextrose from a dextrose containing liquor wherein the primary mode of nucleation is secondary which comprises:
   continuously introducing a dextrose-containing feed liquor at a predetermined rate into a first reaction zone comprised substantially of a lean phase massecuite having a crystal phase content between about 15% and about 45% alpha monohydrate dextrose;
   continuously agitating said first reaction zone at an impeller tip speed rate of from about 60 cm/sec to about 600 cm/sec, said rate being characterized high enough to promote good mixing of the feed liquor with said lean phase massecuite within said first reaction zone and to assure a linear crystal growth rate which is surface reaction controlled and low enough to avoid excessive attrition of said lean phase massecuite within said first reaction zone;
   continuously crystallizing said feed liquor within said first reaction zone to form additional lean phase massecuite, said first reaction zone operating at a constant temperature between about 40° C. and about 50° C., the mean residence time of said feed liquor in said first reaction zone being from about 6 hours to about 30 hours; and
   continuously withdrawing lean phase massecuite from said first reaction zone.

2. A process as defined in claim 1 further including the step of separating a dry sugar and a mother liquor stream from said lean phase massecuite.

3. A process as defined in claim 1 further including the steps of:
   immediately introducing said lean phase massecuite from said first reaction zone into a second reaction zone until said second reaction zone is essentially comprised of said lean phase massecuite;
   continuously agitating said second reaction zone with cooling coils at a rate at which excessive crystal attrition is avoided while heat is transferred between the coils and the bulk of the massecuite;
   crystallizing said lean phase massecuite within said second reaction zone at a crystallization temperature from about 35° C. to about 50° C. for a time period sufficient to form a rich phase massecuite having a crystal phase content above about 60% alpha-monohydrate dextrose, the temperature of crystallization being lowered from a preselected initial value to a preselected final value during said time period; and
   separating alpha-monhydrate dextrose crystals from said rich phase massecuite by removal of mother liquor.

4. A process as defined in claim 1 wherein said rate of agitation is provided by use of an impeller tip speed of about 60 cm/sec.

5. A process as defined in claim 1 wherein said rate of agitation is provided by use of an impeller tip speed between about 300 cm/sec and about 600 cm/sec.